United States Patent [19]

Bosies et al.

[11] Patent Number: 5,002,937
[45] Date of Patent: Mar. 26, 1991

[54] DIPHOSPHONIC ACID COMPOUNDS AND USE FOR CALCIUM METABOLISM DISORDERS

[75] Inventors: Elmar Bosies, Weinheim; Harald Zilch, Mannheim, both of Fed. Rep. of Germany

[73] Assignee: Boehringer Mannheim GmbH, Mannheim, Fed. Rep. of Germany

[21] Appl. No.: 375,747

[22] Filed: Jul. 5, 1989

[30] Foreign Application Priority Data

Jul. 5, 1988 [DE] Fed. Rep. of Germany ....... 3822650

[51] Int. Cl.$^5$ ............................ C07F 9/38; C07F 9/40; A61K 31/66; A61K 31/045
[52] U.S. Cl. ..................................... 514/108; 514/80; 514/82; 514/85; 514/86; 514/89; 514/90; 514/91; 514/94; 514/107; 544/59; 544/243; 544/337; 546/22; 546/23; 548/112; 548/113; 562/13
[58] Field of Search ..................... 562/13; 558/159; 544/59, 243, 337; 546/22, 23; 548/112, 113; 514/80, 82, 85, 86, 89, 90, 91, 94, 107, 108

[56] References Cited

U.S. PATENT DOCUMENTS

| | | | |
|---|---|---|---|
| 4,473,560 | 9/1984 | Biere et al. | 514/107 |
| 4,503,049 | 3/1985 | Biere et al. | 548/113 |
| 4,666,895 | 5/1987 | Bosies et al. | 546/22 |
| 4,687,767 | 8/1987 | Bosies et al. | 546/22 |
| 4,732,998 | 3/1988 | Binderup | 562/13 |
| 4,746,654 | 5/1988 | Breliere et al. | 514/108 |
| 4,777,163 | 10/1988 | Bosies et al. | 548/112 |
| 4,810,486 | 3/1989 | Kelly et al. | 562/13 |

FOREIGN PATENT DOCUMENTS

| | | | |
|---|---|---|---|
| 0186405 | 7/1986 | European Pat. Off. | |
| 273514 | 7/1988 | European Pat. Off. | 546/23 |
| 0274158 | 7/1988 | European Pat. Off. | |
| 304962 | 3/1989 | European Pat. Off. | 546/23 |
| 317505 | 5/1989 | European Pat. Off. | 546/23 |

Primary Examiner—J. E. Evans
Attorney, Agent, or Firm—Felfe & Lynch

[57] ABSTRACT

The present invention provides compounds of the formula:

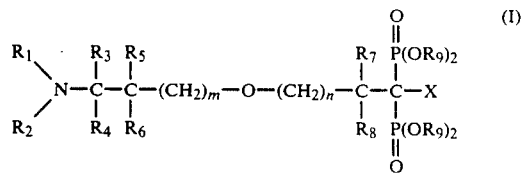

The present invention also provides processes for the preparation of these compounds and pharmaceutical compositions containing them useful in treatment and prophylaxis of disorders of calcium metabolism.

8 Claims, No Drawings

DIPHOSPHONIC ACID COMPOUNDS AND USE FOR CALCIUM METABOLISM DISORDERS

The present invention is concerned with new diphosphonic acid derivatives, processes for the preparation thereof and pharmaceutical compositions containing them.

Federal Republic of Germany Patent Specification No. 18 13 659 describes diphosphonic acid derivatives of which 1-hydroxyethane-1,1-diphosphonic acid has achieved importance for the treatment of Paget's disease.

In Federal Republic of Germany Patent Specification No. 25 34 391 are described aminoalkane-1,1diphosphonic acids which can be substituted on the nitrogen atom by $C_1$-$C_3$-alkyl radicals and which have an action on the calcium metabolism.

Surprisingly, we have now found that aminoalkane-1,1-diphosphonic acids in which the alkyl chain is interrupted by an oxygen atom display a distinctly more marked action on the calcium metabolism than the compounds hitherto known. Thus, these compounds are especially suitable for a wide treatment of calcium metabolism disturbances. In particular, they can be used especially well in cases where the build up and breakdown of bone is disturbed, i.e. they are suitable for the treatment of diseases of the skeletal system, for example osteoporosis, Paget's disease, Bechterew's disease and the like. On the basis of these properties, they can also be used for the therapy of bone metastases, urolithiasis and for the prevention of heteroptopic ossification. Furthermore, due to their influence on the calcium metabolism, they also provide a basis for the treatment of rheumatoid arthritis, of osteoarthritis and of degenerative arthrosis.

Thus, according to the present invention, there are provided diphosphonates of the general formula:

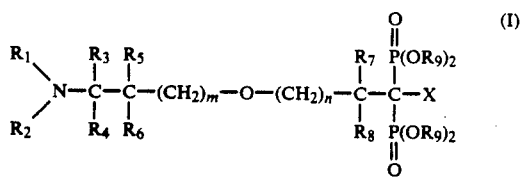

wherein $R_1$ and $R_2$, independently of one another, are hydrogen atoms, straight-chained or branched, saturated or unsaturated alkyl radicals containing up to 9 carbon atoms which can optionally be substituted by hydroxyl, $C_1$-$C_5$-alkoxy or $C_1$-$C_5$-alkylthio, a phenyl or $C_5$-$C_7$-cycloalkyl ring, whereby the phenyl moiety can optionally be substituted by $C_1$-$C_5$-alkyl, $C_1$-$C_5$-alkoxy, hydroxyl or halogen, or are $C_5$-$C_7$-cycloalkyl or phenyl radicals, $R_3$ is a hydrogen atom, a straight-chained or branched $C_1$-$C_5$-alkyl radical, which is optionally substituted by hydroxyl, $C_1$-$C_5$-alkoxy, $C_1$-$C_5$-alkylthio, mercapto, phenyl, 3-indolyl or 4-imidazolyl, or a phenyl radical optionally substituted by hydroxyl or $C_1$-$C_5$-alkoxy, $R_4$, $R_6$, $R_8$ and $R_9$, independently of one another, are hydrogen atoms or $C_1$-$C_5$-alkyl radicals, $R_5$ an $R_7$, independently of one another, are hydrogen atoms, $C_1$-$C_5$-alkyl radicals or phenyl radicals optionally substituted by hydroxyl or $C_1$-$C_5$-alkoxy X is a hydrogen atom, a hydroxyl group or an $-NR_{10}R_{11}$ radical, whereby $R_{10}$ and $R_{11}$, independently of one another, are hydrogen atoms or $C_1$-$C_5$-alkyl radicals and m and n are 0 or 1, whereby $R_1$ and $R_2$, together with the nitrogen atom to which they are attached, can form a mono- or bicyclic ring system containing 4 to 9 carbon atoms which is partly or wholly hydrogenated and optionally substituted by hydroxyl, $C_1$-$C_5$-alkyl or $C_1$-$C_5$-alkoxy and/or, in the case of a monocyclic radical, can be interrupted by an oxygen, nitrogen or sulphur atom, $R_1$ and $R_3$, together with the carbon and nitrogen atoms to which they are attached, can form a five- or six-membered ring which can optionally be condensed by a further six-membered ring, $R_1$ and $R_5$, together with the carbon and nitrogen atoms to which they are attached, as well as the carbon atom lying therebetween, can form a five- or six-membered ring, $R_3$ and $R_4$, together with the carbon atom to which they are attached can form a five- or six-membered ring, $R_4$ and $R_6$, together with the carbon atoms to which they are attached, can form a five- or six-membered ring, $R_5$ and $R_6$, together with the carbon atom to which they are attached, can form a five- or six-membered ring and $R_7$ and $R_8$, together with the carbon atom to which they are attached, can form a five- or six-membered ring; as well as the pharmacologically acceptable salts thereof.

By $C_1$-$C_5$-alkyl radicals are preferably to be understood methyl, ethyl, isopropyl and isobutyl radicals.

$C_1$-$C_5$-alkoxy and alkylthio radicals are preferably methoxy and methylthio radicals, respectively.

The $C_5$-$C_7$-cycloalkyl radical is preferably a cyclohexyl radical.

Halogen is to be understood to be especially a chlorine or bromine atom.

The alkyl chains with up to 9 carbon atoms in the case of $R_1$ and $R_2$ are preferably methyl, ethyl, isopropyl, isobutyl, sec.-butyl, n-pentyl, n-nonyl, allyl or methallyl radicals.

By an alkyl radical substituted by an optionally substituted phenyl radical is to be understood especially a benzyl radical.

The $-NR_{10}R_{11}$ radical is preferably an amino, dimethylamino or diethylamino radical.

If $R_1$ and $R_2$, together with the nitrogen atom to which they are attached, form a ring, then this is preferably understood to be a pyrrolidine, piperidine, di- or octahydroisoindoline or decahydroquinoline ring. A ring interrupted by a heteroatom is preferably a piperazine, morpholine or thiamorpholine ring.

When $R_1$ and $R_3$, together with the nitrogen atom to which they are attached, form a ring, then this is to be understood to be, int.r alia, a pyrrolidine, piperidine or octahydroindole ring substituted in the 2-position.

When $R_1$ and $R_5$, together with the carbon and nitrogen atoms to which they are attached, as well as the carbon atom lying therebetween, form a ring, this ring is preferably a pyrrolidine or piperidine ring substituted in the 3-position.

When $R_3$ and $R_4$ or $R_5$ and $R_6$ or $R_7$ and $R_8$, together with the carbon atom to which they are attached, form a ring, this is preferably a cyclopentyl ring.

If $R_4$ and $R_6$, together with the carbon atoms to which they are attached, form a ring, then this is preferably a cyclohexyl or cyclopentyl ring.

X is preferably a hydrogen atom or a hydroxyl group.

Preferred compounds of formula I are compounds wherein $R_1$ is hydrogen or methyl, $R_2$ is hydrogen or methyl, $R_3$ is hydrogen or $C_1$-$C_5$-alkyl, $R_4$ is hydrogen or methyl, $R_5$ is hydrogen or methyl, $R_6$ is hydrogen, $R_7$ is hydrogen, $R_8$ is hydrogen, $R_9$ is hydrogen, m is zero or 1, n is zero and X is a hydroxyl group whereby $R_1$ and $R_2$ together with the nitrogen atom form a morpholine ring, $R_1$ and $R_3$ together with the carbon and nitrogen atoms to which they are attached form a pyrrolidine or piperidine ring, $R_1$ and $R_5$ together with the carbon and nitrogen atoms to which they are attached form a piperidine ring, $R_4$ and $R_6$ together with the carbon atom to which they are attached form a cyclohexyl ring and $R_5$ and $R_6$ together with the carbon atom to which they are attached form a spiro-cyclopentane ring.

Asymmetric carbon atoms can have the R- or S-configuration and the compounds can be present in the optically-active form or as a racemic mixture. They are also within the scope of the present invention.

Compounds of general formula I are prepared by known processes and preferably by I. mono- or dialkylating a compound of the general formula:

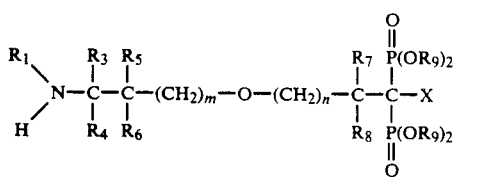

in which $R_1$, $R_3$–$R_9$, X, m and n have the above-given meanings, and optionally saponifying the resulting tetraester to give the corresponding diester or acid of general formula I; or II. when X in general formula I is a hydroxyl group,
(a) reacting a carboxylic acid of the general formula:

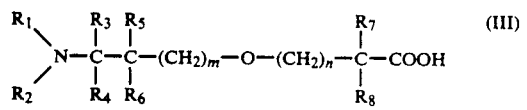

in which $R_1$–$R_8$, m and n have the above-given meanings, with a mixture of phosphorous acid or phosphoric acid and a phosphorus halide or phosphorus oxyhalide and subsequently saponifying to the free diphosphonic acid; or (b) reacting a carboxylic acid chloride of the general formula:

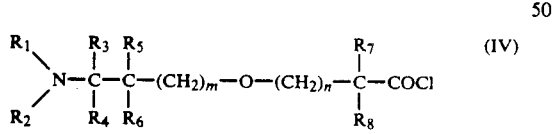

in which $R_1$–$R_8$, m and n have the above-given meanings and in which $R_1$ can also be an acyl radical or, together with $R_2$, can also be a phthaloyl radical as protective group, with a trialkyl phosphite of the general formula:

P(OR')$_3$ (V)

in which R' is an alkyl radical containing up to 4 carbon atoms and preferably a methyl, ethyl, isopropyl or isobutyl radical, to give an acyl phosphonate of the general formula:

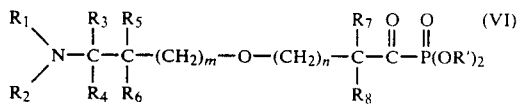

in which $R_1$–$R_8$, m, n and R' have the above-given meanings and $R_1$ can also be an acyl radical or, together with $R_2$, can be a phthaloyl radical, subsequently reacting with a dialkyl phosphite of the general formula:

in which R' has the above-given meaning, to give a disphosphonate of the general formula:

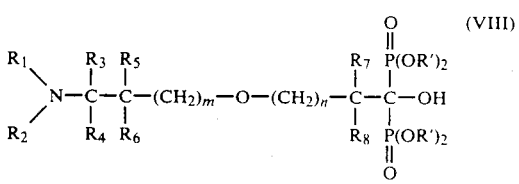

in which $R_1$–$R_8$, m, n and R' have the above-given meanings and $R_1$ can also be an acyl radical or, together with $R_2$, can form a phthaloyl radical, optionally removing the phthaloyl radical by hydrazinolysis and saponifying the resultant tetraester to the corresponding diester or acid of general formula I, whereby, under these conditions, the acyl or phthaloyl radical used as protective group, is simultaneously split off; or (c) when n is 0, reacting a compound of the general formula:

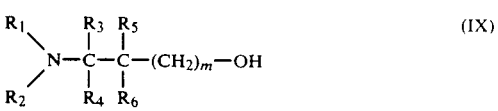

in which $R_1$–$R_6$ and m have the above-given meanings, with an epoxide of the general formula:

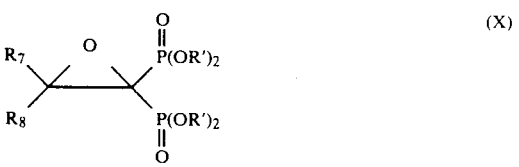

in which $R_7$, $R_8$ and R' have the above-given meanings, and, if desired, saponifying the resultant diphosphonic acid derivative of the general formula:

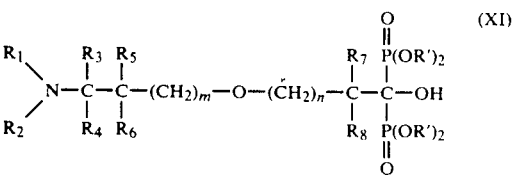

in which $R_1-R_8$, R' and m have the above-given meanings, to the corresponding diester or acid; or III. when X in general formula I is an $-NR_{10}R_{11}$ radical, reacting a carboxylic acid derivative of the general formula:

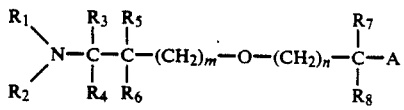
(XII)

in which $R_1-R_8$, m and n have the above-given meanings and A is a nitrile, imino ether or $-CONR_{10}R_{11}$ radical, $R_{10}$ and $R_{11}$ having the above-given meanings, with a phosphorus compound of the general formula:

$$PT_3 \quad \text{(XIII)}$$

in which T is a halogen atom, a hydroxyl group or an OR' radical, R' having the above-given meaning, and possibly saponifying; or IV. when X in general formula I is a hydrogen atom
(a) reacting a compound of the general formula:

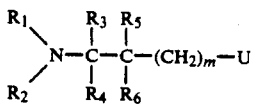
(XIV)

in which $R_1-R_6$ and m have the above-given meanings and $R_1$ can also be an acyl radical or, together with $R_2$, a phthaloyl radical and U is a reactive group, for example a halogen atom or a sulphonate group, with a disphosphinic acid derivative of the general formula:

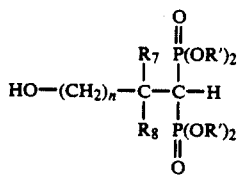
(XV)

in which $R_7$, $R_8$, R' and n have the above-given meanings, optionally removing the phthaloyl radical by hydrazinolysis and optionally saponifying the tetraester formed to the corresponding diester or acid, whereby, under these conditions, the acyl or phthaloyl radical used as protective group, is a simultaneously split off; or (b) adding a compound of the general formula:

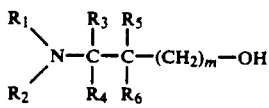
(IX)

in which $R_1-R_6$ and m have the above-given meanings, to a compound of the general formula:

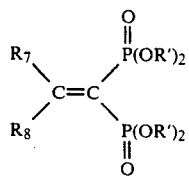
(XVI)

in which $R_7$, $R_8$ and R' have the above-given meaninga, and optionally saponifying the tetraester obtained to the corresponding diester or acid; or (c) reacting a compound of the general formula:

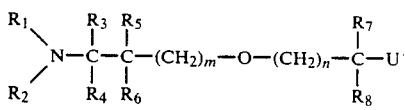
(XVII)

in which $R_1-R_8$, U, m and n have the above-given meanings and $R_1$ can also be an acyl radical or, together with $R_2$, can be a phthaloyl radical, with a disphosphonic acid derivative of the general formula:

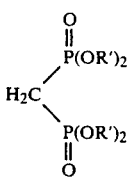
(XVIII)

in which R' has the above-given meaning, removing, if desired, the phthaloyl radical by hydrazinolysis and optionally saponifying the resultant tetraester to the corresponding diester or acid, whereby, under these conditions, the acyl or phthaloyl radical used as protective group is simultaneously split off; or (d) when $R_8$ is a hydrogen atom, catalytically hydrogenating a compound of the general formula:

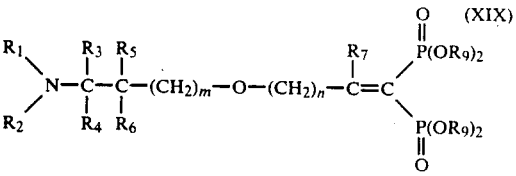
(XIX)

in which $R_1-R_7$, $R_9$, m and n have the above-given meanings and $R_1$ can also be an acyl radical; and subsequently, if desired, saponifying the resultant tetraester to the corresponding diester or acid, whereby acyl radicals possibly present can thereby also be split off at the same time and, if desired, converting a free acid obtained into a pharmacologically acceptable salt.

In the case of the reductive alkylation (process I), a mixture of primary or secondary amines of general formula II and of a carbonyl compound or an acetal thereof is treated in the presence of a hydrogenation catalyst, for example palladium on charcoal or nickel, with hydrogen under atmospheric or elevated pressure or formic acid is used as reducing agent. Furthermore, the alkylation of a secondary amine of general formula I can be carried out especially advantageously by the phase transfer process with dialkyl sulphates.

The carboxylic acids of general formula II used in process II a) are reacted with 1-2 and preferably with 1.5 mole of phosphorous acid or phosphoric acid and 1 to 2 and preferably 1.5 mole of phosphorus trihalide or phosphorus oxyhalide at a temperature of from 80° to 130° C. and preferably of from 100° to 110° C. The reaction can also be carried out in the presence of a diluent, for example a halogenated hydrocarbon and especially chlorobenzene, tetrachloroethane or also sulfolane or dioxan. The subsequent hydrolysis takes place by boiling with water but advantageously with semi-concentrated hydrochloric or hydrobromic acid. As phosphorus trihalides in the above process, there can be used, for example, phosphorus trichloride or phosphorus tribromide and, as phosphorus oxyhalide, especially phosphorus oxychloride.

In the case of process II b), the acid chloride of general formula IV is reacted with the trialkyl phosphite of general formula V at a temperature of from 0° to 60° C. and preferably of from 20° to 40° C. It is possible to work without a solvent or also in the presence of an inert solvent, for example diethyl ether, tetrahydrofuran, dioxan or a halogenated hydrocarbon, for example methylene chloride. The acyl phosphonate of general formula VI obtained as intermediate can be isolated or further reacted directly. The subsequent reaction is carried out in the presence of a weak base, preferably of a secondary amine, for example dibutylamine, at a temperature of from 0° to 60° C. and preferably of from 10° to 30° C. When $R_1$ and $R_2$ together form a phthaloyl radical as protective group, this is split off by hydrazinolysis or acid hydrolysis. In the case of hydrazinolysis, hydrazine is used in acetic acid or also in ethanol at a temperature of from 20° to 80° C. The acidic hydrolysis can be carried out very well by boiling with semi-concentrated hydrochloric acid. In this manner, an acyl radical, preferably an acetyl radical, used as protective group, is also split off.

In the case of process II c), the alcohols of general formula IX are, as a rule, used in the form of their alkali metal salts and preferably as their sodium salts. As solvent, it is preferred to use toluene, dioxan, tetrahydrofuran or also dimethylformamide. The reaction is carried out at a temperature of from 20° to 80° C.

In the case of process III, the nitriles of general formula XII are reacted with phosphorous acid at a temperature of from 110° to 180° C. The reaction can be carried out with a solvent or in the presence of an aprotic solvent, for example diethylene glycol dimethyl ether or diethylene glycol diethyl ether. However, the nitriles can also be reacted with a phosphorus trihalide, for example phosphorus tribromide or phosphorus trichloride, in an inert solvent, for example dioxan or tetrahydrofuran, optionally with the addition of water, at a temperature of from 20° to 80° C. Imino ethers of general formula XII can be reacted with dialkyl phosphites, preferably in the presence of equimolar amounts of sodium, in an inert solvent, for example diethyl ether, dioxan or also benzene, the reaction taking place, as a rule, at the reflux temperature of the solvent employed. Acid amides of general formula XII can be reacted in an inert solvent, for example a halogenated hydrocarbon or an ether, such as diethyl ether, with a mixture of phosphorus pentahalide/phosphorous acid or also of oxalyl chloride/trialkyl phosphite.

In the case of process IV a), the diphosphonic acid derivative of general formula XV is used in the form of a sodium or potassium salt. For this purpose, it is reacted with sodium, potassium or the corresponding hydride in an inert solvent, for example benzene, toluene or dimethylformamide, at a temperature of from 0° to 40° C. and preferably of about 25° C. The alkali metal salt is reacted, without isolation, with the appropriate halide or sulphonate, the temperature thereby used being from 20° to 110° C.

If $R_1$ and $R_2$ together form a phthaloyl radical as protective group or $R_1$ is an acyl radical and preferably an acetyl radical, these radicals are split off in the manner described in process II b).

In the case of process IV b), the alcohols of general formula IX are used in the form of their alkali metal salts and preferably of their sodium salts. For this purpose, they are reacted with sodium or sodium hydride in an inert solvent, for example benzene, toluene, dioxan or dimethylformamide, at a temperature of from 0° to 60° C. and preferably of about 25° C. As a rule, the alkali metal salt is reacted, without isolation, with the appropriate diphosphonate of general formula XVI, the temperature used being from 20° to 80° C.

In the case of process IV c), the methylenediphosphonic acid esters of general formula XVIII are used in the form of their sodium or potassium salts. For this purpose, they are reacted with sodium, potassium or the corresponding hydride in an inert solvent, for example benzene, toluene or dimethylformamide, at a temperature of from 0° to 40° C. and preferably of about 25° C. The alkali metal salt is reacted, without isolation, with the appropriate halide or sulphonate, the temperature used being from 20° to 110° C.

The hydrogenation in the case of process IV d) is carried out in the presence of a noble metal catalyst, for example palladium on charcoal or platinum, in an alcohol, for example methanol or ethanol, as solvent or also in water. However, nickel can also be used in an alkaline medium. The splitting off of the N-acyl radical can be carried out under alkaline conditions but preferably under acidic conditions, for example with 6N hydrochloric acid.

Optically-active compounds of general formula I are usually prepared by using optically-active starting materials.

The aminooxaalkanecarboxylic acids used in process II a) are usually prepared in the following manner: The appropriate aminoalkanol is reacted with, for example, a haloacetic acid ester, to give an aminooxaalkanecarboxylic acid ester which, depending upon the chain length and the substitution on the nitrogen atom, can be cyclised to give an oxalactam. The resultant carboxylic acid ester is saponified in the usual manner under acidic or alkaline conditions. In the case of ring formation, the lactam ring is opened by boiling with barium hydroxide solution and the barium salt of the aminooxaalkanecarboxylic acid is converted into the free acid with sulphuric acid.

The aminoalkanols used in the case of this process, as well as in the case of processes II c) and IV b), are, as a rule, known from the literature or can easily be prepared from the appropriate amino acids or the esters thereof by reduction with, for example lithium aluminium hydride.

The aminooxaalkanecarboxylic acid nitriles or amides used in the case of process III can be synthesised from the appropriate aminoalkanols by reaction with haloacetic acid nitriles or haloacetic acid amides. From the nitriles thus obtained can be obtained the corresponding imino ethers by conventional processes, for example by reaction with a lower alcohol in the presence of gaseous hydrogen chloride.

By the reaction of an aminoalkanol with a phosphorus halide, for example phosphorus trichloride or phosphorus tribromide, or with an aliphatic or aromatic sulphochloride, for example methanesulphochloride or benzenesulphochloride, there is obtained a compound of general formula XIV used in the case of process IV a).

The compounds of general formula XIX used in the case of process IV b) can be prepared, for example, by the elimination of an H—Y group, wherein Y is, for example, a halogen atom, preferably a bromine or chlorine atom, or an acyloxy radical, especially an acetoxy or propionyloxy radical. The elimination can take place.by the use of bases, for example tertiary amines and especially triethylamine, pyridine or diazabicycloundecane, in an inert solvent, for example an alcohol or ether, such as dioxan or tetrahydrofuran. In the case of the splitting off of acetic or propionic acid, there.is preferably used the tetrasodium or tetrapotassium salt of the corresponding diphosphonic acid, the splitting off being carried out by heating to a temperature of from 180° to 300° C. and preferably of from 180° to 240° C. The free acid can be liberated from the tetraalkali metal salt, for example by treatment with an acidic ion exchanger, such as Amberlite IR 120, H+ form.

The above-mentioned starting compounds can be used as racemates or as enantiomers, the opticallyactive compounds usually being obtained from the corresponding optically-active amino acids.

The tetraalkyl esters possibly obtained in the case of the above-mentioned processes can be saponified to the diesters or to the free tetraacids. The saponification to diesters takes place, as a rule, by treating the tetraalkyl esters with an alkali metal halide, preferably with sodium iodide, in an appropriate solvent, for example acetone, at ambient temperature. There is thereby formed the symmetrical diester/disodium salt which can possibly be converted into the diester/diacid by means of an acidic ion exchanger. The saponification to the free diphosphonic acids takes place, as a rule, by boiling with semi-concentrated hydrochloric or hydrobromic acid. However, a splitting off can also be carried out with a trimethylsilyl halide and preferably with the bromide or iodide. On the other hand, the free diphosphonic acids can again be converted into the tetraalkyl esters by boiling with orthoformic acid alkyl esters. The free diphosphonic acids of general formula I can be isolated as free acids or in the form of their mono- or dialkali metal salts. As a rule, the alkali metal salts can be purified by reprecipitation from water/methanol or water/acetone.

As pharmacologically acceptable salts, there are especially used the alkali metal and ammonium salts which are prepared in the usual manner, for example by titration of the compounds with inorganic or organic bases, for example sodium or potassium hydrogen carbonate, aqueous sodium hydroxide solution, aqueous potassium hydroxide solution, aqueous ammonia solution or amines, for example trimethylamine or triethylamine.

The new compounds of general formula I according to the present invention and the salts thereof can be administered enterally or parenterally in liquid or solid form. For this purpose, there can be used all conventional forms of administration, for example tablets, capsules, dragees, syrups, solutions, suspensions and the like. As injection medium, it is preferred to use water which contains the additives usual in the case of injection solutions, for example stabilizing agents, solubilising agents and buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Liquid carrier materials for injection solutions must be sterile and are preferably filled into ampoules. Solid carrier materials include, for example, starch, lactose, mannitol, methylcellulose, talc, highly dispersed silicic acid, high moleculr weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage used can depend upon various factors, for example mode of administration, species, age and/or the individual state of health. The doses to be administered daily are from about 0.1 to 100 mg./human and preferably 1 to 20 mg./human and can be administered divided up one or more times.

Preferred in the sense of the present invention are, apart from the compounds described in the following Examples and compounds which can be derived by the combination of all of the definitions given in the claims, the following diphosphonates, as well as the sodium salts and the methyl, ethyl and isopropyl esters thereof:

5-N,N-dimethylamino-3-oxapentane-1-hydroxy-1, 1-diphosphonic acid

5-N-methyl-N-propylamino-3-oxapentane-1-hydroxy-1, 1-diphosphonic acid

5-N-methyl-N-nonylamino-3-oxapentane-1-hydroxy-1, 1-diphosphonic acid

5-N-benzylamino-3-oxapentane-1-hydroxy-1, 1-diphosphonic acid

5-N-isobutyl-N-methylamino-3-oxapentane-1-hydroxy-1, 1-diphosphonic acid

5-N-methallyl-N-methylamino-3-oxapentane-1-hydroxy-1, 1-diphosphonic acid

5-N-(2-methoxyethyl)-N-methylamino-3-oxapentane-1-hydroxy-1,1-diphosphonic acid

5-N-(2-hydroxyethyl)-N-methylamino-3-oxapentane-1-hydroxy-1,1-diphosphonic acid

5-N-(2-methylthioethyl)-N-methylamino-3-oxapentane-1-hydroxy-1,1-diphosphonic acid 5-N-(4-methylbenzyl)-amino-3-oxapentane-1-hydroxy-1,1-diphosphonic acid 5-N-(2-chlorobenzyl)-amino-3-oxapentane-1-hydroxy-1,1-diphosphonic acid 5-N-cyclohexyl-N-methylamino-3-oxapentane-1-hydroxy-1,1-diphosphonic acid 5-amino-7-methyl-3-oxaoctane-1-hydroxy-1, 1diphosphonic acid 5-amino-6-phenyl-3-oxahexane-1-hydroxy-1, 1-diphosphonic acid 5-amino-6-(3-indolyl)-3-oxahexane-1 -hydroxy-1,1-diphosphonic acid 5-amino-6-(4-imidazolyl)-3-oxahexane-1 -hydroxy-1,1-diphosphonic acid 5-amino-6-hydroxy-3-oxahexane-1-hydroxy-1, 1-diphosphonic acid 5-amino-7-methylthio-3-oxaheptane-1-hydroxy-1, 1-diphosphonic acid 5-N-methyl-N-propylamino-3-oxahexane-1-hydroxy-1,1-diphosphonic acid 5-N-methyl-N-pentylamino-3-oxahexane-1-hydroxy-1,1-diphosphonic acid 5-N-allyl-N-methylamino-3-oxahexane-1-hydroxy-1,1-diphosphonic acid 5-amino-6-(4-hydroxyphenyl)-3-oxahexane-1-hydroxy-1,1-diphosphonic acid 5-amino-4,4-dimethyl-3-oxapentane-1-hydroxy-1,1-diphosphonic acid 5-amino-4-phenyl-3-oxapentane-1-hydroxy-1,1-diphosphonic acid 5-amino-2-methyl-3-oxapentane-1-hydroxy-1,1-diphosphonic acid 5-amino-2,2-dimethyl-3-oxapentane-1-hydroxy-1,1-diphosphonic acid 5-amino-2-phenyl-3-oxapentane-1-hydroxy-1,1-diphosphonic acid 5-(1-pyrrolidinyl)-3-oxapentane-1-hydroxy-1,1-diphosphonic acid 5-(1-piperidinyl)-3-oxapentane-1-hydroxy-1,1-diphosphonic acid 5-(3-hydroxy-1-pyrrolidinyl)-3-oxapentane-1-hydroxy-1,1-diphosphonic acid 5-(3,4-dimethoxy-1-pyrrolidinyl)-3-oxapentane-1-hydroxy-1,1-diphosphonic acid 5-(2,3-dihydroisoindolin-1-yl)-3-oxapentane-1-hydroxy-1,1-diphosphonic acid 5-(octahydroisoindolin-1-yl)-3-oxapentane-1-hydroxy-1,1-diphosphonic acid 5-(decahydroquinolin-1-yl)-3-oxapentane-1-hydroxy-1,1-diphosphonic acid 5-(1-piperazinyl)-3-oxapentane-1-hydroxy-1,1-diphosphonic acid 5-(4-methyl-1-piperazinyl)-3-oxapentane-1-hydroxy-1,1-diphosphonic acid 5-(4-thiamorpholinyl)-3-oxapentane-1-hydroxy-1,1-diphosphonic acid 5-(4-hydroxy-1-piperidinyl)-3-oxahexane-1-hydroxy-1,1-diphosphonic acid S-4-(2-pyrrolidinyl)-3-oxabutane-1-hydroxy-1,1-diphosphonic acid 4-(2-piperidinyl)-3-oxabutane-1-hydroxy-1,1-diphosphonic acid 4-(1-methyl-2-piperidinyl)-3-oxabutane-1-hydroxy-1,1-diphosphonic acid 5-(1-methyl-2-piperidinyl)-3-oxapentane-1-hydroxy-1,1-diphosphonic acid 4-(octahydroindolin-2-yl)-3-oxabutane-1-hydroxy-1,1-diphosphonic acid 4-(1-ethyl-2-pyrrolidinyl)-3-oxabutane-1-hydroxy-1,1-diphosphonic acid 3-(3-pyrrolidinyl)-3-oxapropane-1-hydroxy-1,1-diphosphonic acid 5-amino-5,5-butylene-3-oxapentane-1-hydroxy-1,1-diphosphonic acid 5-N,N-dimethylamino-5,5-pentylene-3-oxapentane-1-hydroxy-1,1-diphosphonic acid 4-(2-aminocyclohexyl)-3-oxabutane-1-hydroxy-1,1-diphosphonic acid 3-(2-aminocyclopentyl)-3-oxapropane-1-hydroxy-1,1-diphosphonic acid 4-(2-aminocyclopentyl)-3-oxabutane-1-hydroxy-1,1-diphosphonic acid 4-(2-N,N-dimethylaminocyclohexyl)-3-oxabutane-1-hydroxy-1,1-diphosphonic acid 5-amino-4,4-butylene-3-oxapentane-1-hydroxy-1,1-diphosphonic acid 6-amino-2,2-butylene-3-oxahexane-1-hydroxy-1,1-diphosphoric acid 5-N,N-dimethylamino-2,2-pentylene-3-oxapentane-1-hydroxy-1,1-diphosphonic acid 1,5-diamino-3-oxapentane-1,1-diphosphonic acid 5-amino-1-N,N-diethylamino-3-oxahexane-1,1-diphosphonic acid 5-amino-3-oxahexane-1,1-diphosphonic acid R-5-amino-3-oxahexane-1,1-diphosphonic acid S-5-amino-3-oxahexane-1,1-diphosphonic acid 5-N,N-dimethylamino-3-oxapentane-1,1-diphosphonic acid R-5-amino-7-methyl-3-oxaoctane-1-hydroxy-1,1-diphosphonic acid R-5-amino-6-phenyl-3-oxahexane-1-hydroxy-1,1-diphosphonic acid S-5-amino-6-phenyl-3-oxahexane-1-hydroxy-1,1-diphosphonic acid R-5-amino-6-(3-indolyl)-3-oxahexane-1-hydroxy-1,1-diphosphonic acid S-5-amino-6-(3-indolyl)-3-oxahexane-1-hydroxy-1,1-diphosphonic acid R-5-amino-6-(4-imidazolyl)-3-oxahexane-1-hydroxy-1,1-diphosphonic acid S-5-amino-6-(4-imidazolyl)-3-oxahexane-1-hydroxy-1,1-diphosphonic acid R-5-amino-1,6-dihydroxy-3-oxahexane-1,1-diphosphonic acid S-5-amino-1,6-dihydroxy-3-oxahexane-1,1-diphosphonic acid R-5-amino-7-methylthio-3-oxaheptane-1-hydroxy-1,1-diphosphonic acid S-5-amino-7-methylthio-3-oxaheptane-1-hydroxy-1,1-disphosphonic acid R-5-N-methyl-N-propylamino-3-oxahexane-1-hydroxy-1,1-diphosphonic acid S-5-N-methyl-N-propylamino-3-oxahexane-1-hydroxy-1,1-diphosphonic acid R-5-N-methyl-N-pentylamino-3-oxahexane-1-hydroxy-1,1-diphosphonic acid S-5-N-methyl-N-pentylamino-3-oxahexane-1-hydroxy-1,1-disphosphonic acid R-5-N-allyl-N-methylamino-3-oxahexane-1-hydroxy-1,1-diphosphonic acid S-5-N-allyl-N-methylamino-3-oxahexane-1-hydroxy-1,1-diphosphonic acid R-5-amino-5-6-(4-hydroxyphenyl)-3-oxahexane-1-hydroxy-1,1-diphosphonic acid S-5-amino-6-(4-hydroxyphenyl)-3-oxahexane-1-hydroxy-1,1-diphosphonic acid R-5-amino-4-phenyl-3-oxapentane-1-hydroxy-1,1-diphosphonic acid S-5-amino-4-phenyl-3-oxapentane-1-hydroxy-1,1-diphosphonic acid R-5-amino-2-methyl-3-oxapentane-1-hydroxy-1,1-diphosphonic acid S-5-amino-2-methyl-3-oxaheptane-1-hydroxy-1,1-diphosphonic acid R-5-amino-2-phenyl-3-oxapentane-1-hydroxy-1,1-diphosphonic acid S-5-amino-2-phenyl-3-oxapentane-1-hydroxy-1,1-diphosphonic acid 5-amino-2-methyl-3-oxahexane-1-hydroxy-1,1-diphosphonic acid 6-amino-3-oxaheptane-1-hydroxy-1,1-diphosphonic acid 6-amino-5-methyl-3-oxahexane-1-hydroxy-1,1-diphosphonic acid 6-amino-4-methyl-3-oxahexane-1-hydroxy-1,1-diphosphonic acid.

The following Examples show some of the process variants which can be used for the synthesis of the compounds according to the present invention. However, they are not to represent a limitation of the subject matter of the present invention. As a rule, the compounds are obtained as high melting point solid products (mono- or disodium salts), the structures of which have been verified by H, P and possibly by $^{13}$C NMR spectroscopy. The purity of the substances was determined by means of C, H, N, P, S and Na analyses, as well as by thin layer electrophoresis (cellulose, oxalate buffer of pH 4.0). For the characterisation of the individual compounds, there are given the $M_{rel}$ values (relative mobility), referred to pyrophosphate ($M_{rel}=1$).

EXAMPLE 1

R,S-5-Amino-3-oxahexane-1-hydroxy-1, 1-diphosphonic acid 0.67 g. (5 mmol) R,S-5-amino-3-oxahexanoic acid are melted at 100° C. with 0.82 g. (10 mmol) phosphorous acid. The oil bath used is removed, 1 ml. (11 mmol) phosphorus trichloride is added dropwise thereto and heating continued for a further 24 hours at an external temperature of 100° C. After cooling, the reaction mixture is mixed with 10 ml. water, boiled under reflux for 45 minutes and filtered off with suction. The filtrate is concentrated to one half, the solution is adjusted to pH 5 with 10N aqueous sodium hydroxide solution, mixed with 20 ml. methanol and the solution is cooled in an ice-bath. The precipitate obtained is filtered off with suction, washed with methanol and dried. The residue is dissolved in a little water and purified over an ion exchanger column (35 g. Amberlite-IT 120; H+ form). There is obtained 0.49 g. (34% of theory) of the desired compound which contains 0.5 mole of water of crystallisation; m.p. 240°-260° C.; $M_{rel}=0.40$.

The R,S-5-amino-3-oxahexanoic acid used as starting material is prepared in the following way: R,S-5-methylmorpholin-3-one (m.p. 62°-64° C.) is boiled with barium hydroxide and the free acid produced from the barium salt with sulphuric acid at pH 5; m.p. 190°-193° C.

In an analogous manner, by reacting phosphorous acid and phosphorus trichloride with the following starting material, there is obtained:

(a) from R,S-5-N,N-dimethylamino-3-oxahexanoic acid (m.p. 108°-110° C.) (prepared by the reductive methylation of R,S-5-amino-3-oxahexanoic acid by means of formic acid/formaldehyde), R,S-5-N,N-dimethylamino-3-oxahexane-1-hydroxy-1,1-diphosphonic acid as the free acid with 1 mole of water of crystallisation in a yield of 36% of theory; m.p. about 270° C.; $M_{rel}=0.40$.

EXAMPLE 2

Analogously to Example 1, there are obtained, by the use of:

(a) 5-amino-3-oxapentanoic acid (m.p. 188°-190° C.), 5-amino-3-oxapentane-1-hydroxy-1,1-diphosphonic acid with 1 mole water of crystallisation; yield 31% of theory; m.p. 255°-260° C.; $M_{rel}:0.30$.

(b) 6-(N-acetylamino)-3-oxahexanoic acid (oil), 6-amino-3-oxahexane-1-hydroxy-1,1-diphosphonic acid with 1 mole water of crystallisation; yield 23% of theory; m.p. 125°-130° C.; $M_{rel}:0.30$.

(c) 5-N-methylamino-3-oxapentanoic acid (m.p. 242°-245° C.), 5-N-methylamino-3-oxapentane-1-hydroxy-1, 1-diphosphonic acid with 1 mole water of crystallisation; yield 28% of theory; m.p. 155°-160° C.; $M_{rel}:0.35$.

(d) 6-N,N-dimethylamino-3-oxahexanoic acid hydrochloride (oil), 6-N,N-dimethylamino-3-oxahexane-1-hydroxy-1,1-diphosphonic acid with 1 mole water of crystallisation; yield 22% of theory; m.p. 115°-120° C.; $M_{rel}:0.30$.

(e) R-5-amino-3-oxahexanoic acid (m.p. 182°-185° C.; $[\alpha]_D^{20}:-30.5°,c=1.5$ in water), R-5-amino-3-oxahexane-1-hydroxy-1,1-diphosphonic acid with 1 mole water of crystallisation; yield 30% of theory; m.p. 118°-123° C.; $[\alpha]_D^{20}: -22.6°$, c=0.8 in water; $M_{rel}: 0.30$.

(f) S-5-amino-3-oxahexanoic acid (m.p. 180°-182° C.; $[\alpha]_D^{20}:-28.5°,c=1.4$ in water), S-5-amino-3-oxahexane-1-hydroxy-1,1-diphosphonic acid with 1 mole water of crystallisation; yield 34% of theory; m.p. 115°-120° C.; $[\alpha]_D^{20}:+21.2°,c=0.8$ in water; $M_{rel}:0.30$.

(g) 5-amino-6-methyl-3-oxaheptanoic acid (oil), 5-amino-6-methyl-3-oxaheptane-1-hydroxy-1, 1-diphosphonic acid with 1 mole water of crystallisation; yield 22% of theory; m.p. 135°-140° C.; $M_{rel}:0.35$.

(h) S-5-amino-6-methyl-3-oxaheptanoic acid (m.p. 140°-145° C.; $[\alpha]_D^{20}: +23.9°,c=1$ in water, S-5-amino-6-methyl-3-oxaheptane-1-hydroxy-1, 1-diphosphonic acid with 1 mole water of crystallisation; yield 27% of theory; m.p. 245°-250° C.; $[\alpha]_D^{20}:+19.3°,c=1.0$ in water; $M_{rel}:0.30$.

(i) R-5-amino-6-methyl-3-oxaheptanoic acid (m.p. 143°-147° C.; $[\alpha]_D^{20}:-24.3°$, c=1.1 in water), R-5-amino-6-methyl-3-oxaheptane-1-hydroxy-1, 1-diphosphonic acid with 1 mole water of crystallisation; yield 26% of theory; m.p. 245°-250° C.; $[\alpha]_D^{20}:-18.9°,c=1.0$ in water; $M_{rel}:0.30$.

(j) S-5-amino-7-methyl-3-oxaoctanoic acid; m.p. 148°-150° C.; $[\alpha]_D^{20}: +17.7°,c=1.2$ in water), S-5-amino-7-methyl-3-oxaoctane-1-hydroxy-1, 1-diphosphonic acid with 1 mole water of crystallisation; yield 31% of theory; m.p. 250°-255° C.; $M_{rel}:0.30$.

(k) 5-amino-5-methyl-3-oxahexanoic acid (m.p. 243°-245° C., 5-amino-5-methyl-3-oxahexane-1-hydroxy-1,1-diphosphonic acid with 1 mole water of crystallisation; yield 27% of theory; m.p. 155°-160° C.; $M_{rel}:0.40$.

(l) 5-amino-4-methyl-3-oxapentanoic acid (m.p. 213°-215° C.), 5-amino-4-methyl-3-oxapentane-1-hydroxy-1, 1-diphosphonic acid with 1 mole water of crystallisation; yield 33% of theory; m.p. 145°-150° C.; $M_{rel}:0.30$.

(m) 5-(4-morpholinyl)-3-oxapentanoic acid hydrochloride (oil), 1-hydroxy-5-(4-morpholinyl)-3-oxapentane-1, 1-diphosphonic acid with 1 mole water of crystallisation; yield 28% of theory; m.p. 135°-140° C.; $M_{rel}:0.35$.

(n) 3-(N-acetyl-3-piperidinyl)-3-oxapropionic acid (oil), 1-hydroxy-(3-piperidinyl)-3-oxapropane-1, 1diphosphonic acid with 1 mole water of crystallisation; yield 15% of theory; m.p. 185°-190° C.; $M_{rel}:0.30$.

(o) 3-(2-aminocyclohexyl)-3-oxapropionic acid (m.p. 218°-220° C.), 3-(2-aminocyclohexyl)-3-oxapropane-1-hydroxy-1, 1-diphosphonic acid with 1 mole water of crystallisation; yield 19% of theory; m.p. 215°-220° C.; $M_{rel}:0.25$.

(p) 5-amino-4,4-pentylene-3-oxapentanoic acid (m.p. 203°-205° C.), 5-amino-4,4-pentylene-3-oxapentane-1-hydroxy-1, 1-diphosphonic acid with 1 mole water of crystallisation; yield 29% of theory; m.p. 235°-240° C.; $M_{rel}$:0 30.

(q) S-4-(2-pyrrolidinyl)-3-oxabutyric acid (m.p. 152°-155° C.; $[\alpha]_D^{20}$:+20.3°,c=1.3 in water, S-1-hydroxy-4-(2-pyrrolidinyl)-3-oxabutane-1, 1diphosphonic acid with 1 mole water of crystallisation; yield 26% of theory; m.p. 120°-125° C., [$\alpha$ $_D^{20}$:+18.0°,c=0.9 in water; $M_{rel}$:0.30.

(r) R-5-amino-4-methyl-3-oxapentanoic acid (m.p. 210°-212° C.; $[\alpha]_D^{20}$:−97.0°,c=1 in water), R-5-amino-4-methyl-3-oxapentane-1-hydroxy-1, 1-diphosphonic acid with 1 mole water of crystallisation; yield 23% of theory; m.p. 140°-145° C.; $[\alpha]_D^{20}$:−22.5°,c=1 in water; $M_{rel}$:0.30.

(s) S-5-amino-4-methyl-3-oxapentanoic acid (m.p. 212°-214° C.; $[\alpha]_D^{20}$:+97.8°,c=1 in water , S-5-amino-4-methyl-3-oxapentane-1-hydroxy-1, 1-diphosphonic acid with 1 mole water of crystallisation; yield 15% of theory; m.p. 145°-150° C.; $[\alpha]_D^{20}$:+22.9°,c=1 in water, $M_{rel}$:0.30.

(t) 4-(2-piperidinyl)-3-oxabutyric acid (m.p. 158°-160° C.), 1-hydroxy-4 -(2-piperidinyl)-3-oxabutane-1,1-diphosphonic acid with 1 mole water of crystallisation; yield 24% of theory; m.p. 175°-180° C.; $M_{rel}$:0.30.

The 5-amino-3-oxapentanoic acid used in Example 2a) is prepared in the following way:

Ethanolamine is reacted in the presence of sodium hydride with ethyl chloroacetate to give morpholin-3-one (m.p. 100°-102° C.) and the desired acid obtained therefrom by heating with barium hydroxide and subsequent treatment with sulphuric acid.

The intermediate products set out in the following Table are prepared and reacted in an analogous manner:

| Example No. | Morpholinone | m.p. °C. | $[\alpha]_D^{20}$ in methanol |
|---|---|---|---|
| 2 c | N-methylmorpholin-3-one | oil | — |
| 2 e | R-5-methylmorpholin-3-one | 60–62 | −3.7° |
| 2 f | S-5-methylmorpholin-3-one | 59–61 | +3.1° |
| 2 g | 5-isopropylmorpholin-3-one | 86–88 | — |
| 2 h | S-5-isopropylmorpholin-3-one | 86–88 | +3.9° |
| 2 i | R-5-isobutylmorpholin-3-one | 87–89 | −4.3° |
| 2 j | S-5-isobutylmorpholin-3-one | 70–72 | −4.0° |
| 2 k | 5,5-dimethylmorpholin-3-one | 133–35 | — |
| 2 l | 6-methylmorpholin-3-one | 96–98 | — |
| 2 o | 2-oxa-5-azabicyclo[4.4.0]-decan-4-one | 174–76 | — |
| 2 p | 1-oxa-4-azabicyclospiro-[5.5]undecan-3-one | 93–95 | — |
| 2 q | S-3-oxa-6-azabicyclo[4.3.0]-nonan-5-one | 64–66 | — |
| 2 r | R-6-methylmorpholin-3-one | 96–98 | −134.1° |
| 2 s | S-6-methylmorpholin-3-one | 95–97 | +131.1° |
| 2 t | 3-oxa-6-azabicyclo[4.4.0]-decan-5-one | oil | — |

In the case of Examples 2b) and 2n), the starting aminoalcohols are first acetylated on the nitrogen atom, subsequently reacted in the presence of sodium hydride with ethyl bromoacetate to give the corresponding ethyl alkoxyacetate and then saponified with an aqueous solution of sodium hydroxide. All the intermediates are obtained in the form of an oil.

In the case of Examples 2d) and 2m), the tert.-aminoalcohols are reacted in the presence of sodium hydride with ethyl bromoacetate (2m)) or with the sodium salt of chloroacetic acid (2d)), in the latter case esterified with ethanol-sulphuric acid to the corresponding ethyl ester and in both cases subsequently saponified with 2N hydrochloric acid. Here, too, all the intermediates are obtained in the form of an oil.

EXAMPLE 3

5-Amino-3-oxapentane-1,1-diphosphonic acid 1.73 g. (6 mmol) Methanediphosphonic acid tetraethyl ester is added dropwise to 144 mg. (6 mmol) sodium hydride in 5 ml. anhydrous toluene. After completion of the evolution of hydrogen, stirring is continued for 30 minutes and then 1.7 g. (6 mmol) N-(2-bromoethoxyethyl)-phthalimide (m.p. 83°-85° C.) is added dropwise thereto. The reaction mixture is stirred for 24 hours at ambient temperature, then mixed with water, the aqueous phase is adjusted to pH 5 with 2N hydrochloric acid and the organic phase is separated off, dried and evaporated. The residue is purified over 250 g. silica gel (elution agent: methylene chloride/methanol 4/1 v/v) to give 0.35 g. (12% of theory) 5-phthalimido-3-oxapentane-1,1-diphosphonic acid tetraethyl ester in the form of an oily substance. The ester is subsequently boiled under reflux for 12 hours with 10 ml. 6N hydrochloric acid and, after cooling, the precipitated phthalic acid is filtered off with suction. The residue is taken up in water, the solution is adjusted with 2N aqueous sodium hydroxide solution to pH 5 and mixed, while cooling with ice, with a large excess of methanol. The precipitate obtained is filtered off with suction and dried. There is obtained 0.125 g. (7.2% of theory) of the desired compound in the form of the monosodium salt containing 1 mole water of crystallisation; m.p.>300° C.; $M_{rel}$=0.30.

It will be understood that the specification and examples are illustrative but not limitative of the present invention and that other embodiments within the spirit and scope of the invention will suggest themselves to those skilled in the art.

The test data shows general use in treatment and/or prophylaxis for disorders of calcium metabolism. Thus the test serves as a general reference to demonstrate an effect on disturbances of calcium metabolism and is not to be limited to a specific disorder.

Test Report

Male Wistar rats from our own breeding weighing about 160 g were thyroparathyroidectomized on day 1. On day 5, the success of the operation was controlled y measuring calcemia after a night fasting. From that day on, all the animals were group-fed, that means all of them ate the same quantity of food. Furthermore, the animals received then daily for 3 days 2 subcutaneous injections, on containing 25/ug of a synthetic retinoid, the other one the bisphosphonate to be tested, Additionally, all animals were given 2/ug of thyroxine the first and last day of treatment. 24 h after the last injection of the retinoid and the bisphosphonate and after one night fasting, blood was taken by retroorbital puncture under ether anesthesia. Plasma calcium was then analyzed by means of atomic absorption.

The table shows the various doses compared with 4-amino-1-hydroxy-butan-1,1-diphosphonic acid.

| Example | mg P/kg | | | |
| | 0.0003 | 0.001 | 0.01 | 0.1 |
|---|---|---|---|---|
| 1 | + | +++ | ++++ | ++++ |
| 2 e | (+) | +++ | ++++ | |
| 2 f | + | +++ | ++++ | |

-continued

| Example | mg P/kg | | |
|---|---|---|---|
| | 0.0003 | 0.001 | 0.01 | 0.1 |
| 2 k | | (+) | +++ | |
| 2 l | | + | +++ | |
| 2 o | | ++ | +++ | |
| A | | 0 | + | +++ |

0 = Depression of Hypercalaemie −0.99 bis +0.99 mg %
(+) = Depression of Hypercalaemie 1.0 bis 1.99 mg %
+ = Depression of Hypercalaemie 2.0 bis 2.99 mg %
++ = Depression of Hypercalaemie 3.0 bis 3.99 mg %
+++ = Depression of Hypercalaemie 4.0 bis 4.99 mg %
++++ = Depression of Hypercalaemie >5.0
A = 4-amino-1-hydroxybutan-1,1-diphosphonic acid. (US 4 407 761)

We claim:

1. A compound of the formula:

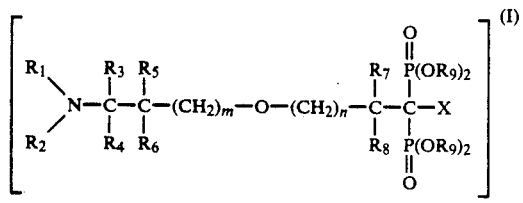

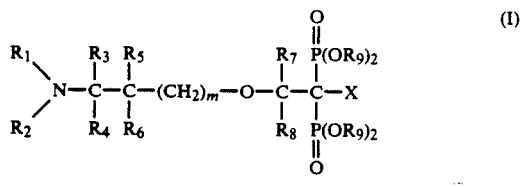

wherein $R_1$ is hydrogen or methyl, $R_2$ is hydrogen or methyl, $R_3$ is hydrogen or $C_1$-$C_5$-alkyl, $R_4$ is hydrogen or methyl, $R_5$ is hydrogen or methyl, $R_6$ is hydrogen, $R_7$ is hydrogen, $R_8$ is hydrogen, $R_9$ is hydrogen, m is zero or 1 and X is a hydroxyl group or wherein $R_1$ and $R_2$ together with the nitrogen atom to which they are attached form a morpholine ring, or $R_1$ and $R_3$ together with the carbon and nitrogen atoms to which they are attached form a pyrrolidine or piperidine ring, or $R_1$ and $R_5$ together with the carbon and nitrogen atoms to which they are attached form a piperidine ring, or $R_4$ and $R_6$ together with the carbon atom to which they are attached form a cyclohexyl ring or $R_5$ and $R_6$ together with the carbon atom to which they are attached form a spirocyclopentane ring as well as the pharmacologically acceptable salts thereof and the optical isomers thereof.

2. The compound of claim 1 designated R,S-5-Amino-3-oxahexane-1-hydroxy-1,1-diphosphonic acid; R-5-amino-3-oxahexane-1-hydroxy-1,1-diphosphonic acid; S-5-amino-3-oxahexane-1-hydroxy-1,1-diphosphonic acid; 5-amino-5-methyl-3-oxahexane-1-hydroxy-1,1-diphosphonic acid; 5-amino-4-methyl-3-oxapentane-1-hydroxy-1,1-diphosphonic acid; and 3-(2-aminocyclohexyl)-3-oxapropane-1-hydroxy-1,1-diphosphonic acid.

3. A pharmaceutical composition for the treatment of calcium metabolism disorders comprising an effective amount of at least one compound of the formula of claim 1 in a pharmaceutically acceptable carrier.

4. A pharmaceutical composition for the treatment of calcium metabolism disorders comprising an effective amount of at least one compound of claim 2 in a pharmaceutically acceptable carrier.

5. A method for the treatment or prophylaxis of disorders of calcium metabolism comprising administering at least one of a pharmaceutically effective compound of claim 1 in a pharmaceutically acceptable carrier to a patient in need of said treatment.

6. A method for the treatment or prophylaxis of disorders of calcium metabolism comprising administering at least one of a pharmaceutically acceptable compound of claim 2 in a pharmaceutically acceptable carrier to a patient in need of said treatment.

7. The method of claim 5 wherein the dose is 0.001–10 mg P/kg.

8. The method of claim 6 wherein the dose is 0.001–10 mg P/kg.

* * * * *

UNITED STATES PATENT AND TRADEMARK OFFICE
CERTIFICATE OF CORRECTION

PATENT NO. : 5,002,937
DATED : March 26, 1991
INVENTOR(S) : Elmar Bosies, et al.

It is certified that error appears in the above-identified patent and that said Letters Patent is hereby corrected as shown below:

Col. 2, line 49, change "int.r alia" to -- inter alia --.

Col. 6, line 11, change "meaninga" to -- meanings --.

Col. 9, line 16, change "place.by" to -- place by --.

Col. 14, line 41, after "m.p. 250°-255°C.;" insert -- $[\alpha]_D^{20}$: + 14.8°, c=1.2 in water; --.

Col. 16, line 47, change "controlled y" to -- controlled by --.

Signed and Sealed this

Thirtieth Day of March, 1993

*Attest:*

STEPHEN G. KUNIN

*Attesting Officer*  Acting Commissioner of Patents and Trademarks